(12) United States Patent
Mantelle et al.

(10) Patent No.: US 7,993,671 B2
(45) Date of Patent: Aug. 9, 2011

(54) TRANSDERMAL COMPOSITIONS CONTAINING LOW MOLECULAR WEIGHT DRUGS WHICH ARE LIQUID AT ROOM TEMPERATURES

(75) Inventors: Juan Mantelle, Miami, FL (US); David Houze, Coconut Grove, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 1060 days.

(21) Appl. No.: 09/986,945

(22) Filed: Nov. 13, 2001

(65) Prior Publication Data

US 2002/0058058 A1    May 16, 2002

Related U.S. Application Data

(63) Continuation of application No. 08/578,308, filed on Dec. 26, 1995, now Pat. No. 6,316,022, which is a continuation of application No. 08/472,759, filed on Jun. 7, 1995, now abandoned.

(51) Int. Cl.
*A61K 9/70* (2006.01)
*A61K 31/785* (2006.01)
*A61L 15/16* (2006.01)

(52) U.S. Cl. .............. 424/449; 424/448; 424/78.16

(58) Field of Classification Search .............. 424/448, 424/444
See application file for complete search history.

(56) References Cited

U.S. PATENT DOCUMENTS

| | | | |
|---|---|---|---|
| 4,814,168 A | 3/1989 | Sablotsky et al. | |
| 4,828,875 A | 5/1989 | Im et al. | 514/534 |
| 4,861,800 A | 8/1989 | Buyske | 514/648 |
| 4,868,218 A | 9/1989 | Buyske | 514/848 |
| 4,880,833 A | 11/1989 | Knoll et al. | 514/566 |
| 4,886,164 A | 12/1989 | Stein et al. | 514/649 |
| 4,994,267 A | 2/1991 | Sablotsky | |
| 4,999,382 A | 3/1991 | Wurtman et al. | 514/648 |
| 5,071,645 A | 12/1991 | Johnson et al. | 424/486 |
| 5,075,338 A | 12/1991 | Knoll et al. | 514/854 |
| 5,151,419 A | 9/1992 | Perenyi et al. | 614/228 |
| 5,151,449 A | 9/1992 | Milgram | 514/654 |
| 5,179,126 A | 1/1993 | Wurtman et al. | 614/848 |
| 5,180,783 A | 1/1993 | Seguela et al. | 424/473 |
| 5,189,084 A | 2/1993 | Birbaum et al. | 614/681 |
| 5,192,560 A | 3/1993 | Umetsu et al. | 424/473 |
| 5,192,808 A | 3/1993 | Ruehl et al. | 514/654 |
| 5,204,116 A | 4/1993 | Edgren et al. | 428/473 |
| 5,220,088 A | 6/1993 | Fujiwara et al. | 664/381 |
| 5,223,540 A | 6/1993 | Wurtman et al. | 514/840 |
| 5,230,898 A * | 7/1993 | Horstmann et al. | 424/449 |
| 5,234,957 A | 8/1993 | Mantelle | 514/772.8 |
| 5,242,950 A | 9/1993 | Fries Hastings | 514/654 |
| 5,254,349 A | 10/1993 | Dong et al. | 424/473 |
| 5,268,332 A | 12/1993 | Alugbin et al. | 424/473 |
| 5,284,660 A * | 2/1994 | Lee et al. | 424/449 |
| RE34,579 E | 4/1994 | Buyske et al. | 514/646 |
| 5,300,291 A | 4/1994 | Sablotsky et al. | |
| 5,320,597 A | 6/1994 | Sage, Jr. et al. | 804/20 |
| 5,320,598 A | 6/1994 | Haak et al. | 804/20 |
| 5,320,850 A | 6/1994 | Gale et al. | 424/449 |
| 5,378,473 A | 1/1995 | Sharma et al. | 424/449 |
| 5,474,783 A * | 12/1995 | Miranda et al. | 424/448 |
| 5,527,536 A | 6/1996 | Merkle et al. | |
| 5,656,286 A * | 8/1997 | Miranda et al. | 424/449 |
| 5,830,505 A | 11/1998 | Fischer et al. | |
| 6,057,321 A | 5/2000 | Lochead et al. | 424/413 |
| 6,128,146 A | 10/2000 | Ngo | 424/473 |
| 6,200,196 B1 | 3/2001 | Custer et al. | 424/473 |
| 6,221,538 B1 | 4/2001 | Kerszykowski et al. | 424/473 |
| 6,226,448 B1 | 5/2001 | Takagi et al. | 514/664 |
| 6,278,067 B1 | 8/2001 | Allen et al. | 514/648 |
| 6,304,379 B1 | 10/2001 | Kobayashi | 424/449 |
| 6,316,022 B1 * | 11/2001 | Mantelle et al. | 424/448 |

FOREIGN PATENT DOCUMENTS

| | | |
|---|---|---|
| EP | 2022522 | 2/1992 |
| EP | 0 473 252 | 3/1992 |
| EP | 0 500 781 | 10/1992 |
| EP | 0524776 A1 * | 1/1993 |
| EP | 0 593 807 | 4/1994 |
| EP | 0 593 807 A1 | 4/1994 |
| JP | 56-108707 | 8/1981 |
| JP | 61-261819 | 11/1988 |
| JP | 2-255611 | 10/1990 |
| WO | 89/09051 | 10/1989 |
| WO | 91/18692 | 12/1992 |
| WO | 92/21333 | 12/1992 |
| WO | WO 9300058 A1 * | 1/1993 |
| WO | 93/21894 | 11/1993 |
| WO | WO 94/02123 | 2/1994 |
| WO | 94/08671 | 4/1994 |
| WO | WO 94/23707 | 10/1994 |

* cited by examiner

*Primary Examiner* — Michael G Hartley
*Assistant Examiner* — Nabila Ebrahim
(74) *Attorney, Agent, or Firm* — Foley & Lardner LLP

(57) ABSTRACT

A transdermal composition is disclosed which contains a blend of one or more polymers, one or more drugs, at least one of which has a low molecular weight and is liquid at or about room temperatures. The composition is substantially free of water and liquids which have a normal boiling point (a) optionally below processing temperatures and (b) greater than or equal to the temperature of the low molecular weight drugs. The composition does not suffer from the substantial loss of the lower molecular weight drug during production of the transdermal system. A transdermal composition is also disclosed which has one or more drugs, at least one of which has a low molecular weight and is liquid at or about room temperatures, and a polymer matrix including one or more high shear resistant polymers. The high shear resistant polymer(s) reduce the plasticizing effect of the low molecular weight drug, and has sufficient tack and shear for application to a human being.

6 Claims, 1 Drawing Sheet

TRANSDERMAL COMPOSITIONS CONTAINING LOW MOLECULAR WEIGHT DRUGS WHICH ARE LIQUID AT ROOM TEMPERATURES

CROSS-REFERENCE TO RELATED APPLICATIONS

This is a Continuation application of Ser. No. 08/578,308, filed Dec. 26, 1995, now U.S. Pat. No. 6,316,022 which is, in turn, a Continuation application of Ser. No. 08/472,759, filed Jun. 7, 1995, now abandoned.

BACKGROUND OF THE INVENTION

1. Field of the Invention

The present invention is directed to a transdermal drug delivery system containing low molecular weight drugs which are liquid at or about room temperatures, its method of making and method of use. In particular, the present invention is directed to a transdermal drug delivery system for the transdermal application of one or more drugs, which during processing is substantially free of water and liquids which have a normal boiling point (a) optionally below processing temperatures and (b) greater than or equal to the normal boiling point of the low molecular weight drugs, and to a transdermal drug delivery system which comprises a polymer matrix including high shear resistance polymers.

2. Description of Related Art

The use of a transdermal drug delivery system, for example a pressure-sensitive adhesive containing a medicament, namely, a drug, as a means for administering therapeutically effective amounts of the medicament is well known. Such known delivery systems involve incorporation of a medicament into a carrier such as a polymeric and/or a pressure-sensitive adhesive formulation. The pressure-sensitive adhesive must adhere effectively to the skin and permit migration of the medicament from the carrier through the skin and into the bloodstream of the patient.

The use of low molecular weight drugs, which are generally liquid at or about room temperatures, such as deprenyl [phenyl isopropylmethylpropynylamine, N,∝-dimethyl-N-2-propynyl-benzeneethanamine]: and more particularly the levorotatory form of the compound, also known as L-deprenyl, L-deprenil, L-deprenaline and selegiline and hereinafter referred to broadly as selegiline), in treating human beings or other animals is well known in the art. For example, WO 91/185592 describes the use of selegiline for treating Parkinson's disease and increasing the life-expectancy of human beings. U.S. Pat. No. 5,192,808 describes the use of selegiline in the treatment of Cushing's disease in humans and animals.

The use of low molecular weight drugs such as selegiline, in transdermal compositions is also generally known in the art. For example, European patent application 509,761 and PCT WO 89/09051 describe the use of a transdermal compositions containing selegiline for the treatment of Parkinson's disease. WO 92/21333 describes the use of a transdermal composition containing selegiline for treating withdrawal symptoms and reducing the craving of addictive psychostimulants, addictive opiates, alcohol, or nicotine. The compositions described in WO 89/09051 include a transdermal preparation of a mixture of L-deprenyl in the hydrophilic polymer Eudragit E 100 and a non-swellable acrylate polymer Durotack 28-2416 and a plasticizer such as Brij 97. European patent application no. 473,252 and Canadian patent application no 2,022,552 describe the use of selegiline in transdermal compositions for the treatment of Parkinson's disease. U.S. Pat. No. 5,242,950 describes the use of a transdermal patch containing selegiline for macular degeneration. U.S. Pat. No. 4,868,218 describes the transdermal application of selegiline in the treatment of depression. Nicotine and nitroglycerine are drugs, normally liquid at or about room temperatures, for which there is considerable art on transdermal use.

However, most reported transdermal systems, such as those described above, use drugs having the salt form of a base drug which is less volatile and has a much higher boiling point than the free-base form of the drug. Transdermal drug delivery systems which use the free-base form of the drug, all suffer from the loss of the drug during manufacture of the transdermal system. This loss is due to the volatile nature of the drug during the drying stage in the production of cast systems. European patent application 593,807 describes a transdermal system that attempts to solve the problem of liquid drug loss. However, this transdermal system requires the use of multilayers of polymeric adhesive which contributes toward increased cost and complexity.

Another related problem with liquid, low molecular weight drugs, is the plasticizing effect that the drug has on the polymer matrix in the transdermal drug delivery system. Namely, the low molecular weight base form of the drug has an excessive plasticizing effect on the polymer, resulting in a composition that is "leggy or gummy." This renders the composition unsuitable for adhesion to the epidermis.

SUMMARY OF THE INVENTION

One object of the present invention is to provide a transdermal drug delivery system which does not suffer from the substantial loss of low molecular weight drugs which are liquid at or about room temperatures, during production of the transdermal system. Another object of the present invention is to produce a low molecular weight drug containing transdermal drug delivery system which is simpler in composition and design than the transdermal systems known in the art.

Still another object of the present invention is to provide a high loadable transdermal drug delivery system which contains a therapeutically effective amount of one or more drugs at least one of which is of low molecular weight and liquid at or about room temperatures, but does not excessively plasticize the polymer or polymers of the transdermal drug delivery system.

In accomplishing the foregoing objects, there has been provided according to one aspect of the present invention a pressure sensitive transdermal drug delivery system comprising: a blend of (a) one or more polymers; and (b) a therapeutically effective amount of one or more drugs, at least one of which is of low molecular weight and liquid at or about room temperatures. The system is substantially free of water and liquids having a normal boiling point (a) optionally below processing temperatures and (b) equal to or greater than (≧) the normal boiling points of the low molecular weight drugs.

In another preferred embodiment, the low molecular weight and liquid drug comprises selegiline, especially the free base form. In still another preferred embodiment, the acrylic-based polymer is present in an amount of about 10 to about 90 weight percent (%) based on the dry weight of the total transdermal system. In still another preferred embodiment, the polymer is a pressure-sensitive adhesive, which includes a blend of an acrylic-based polymer and a silicone-based polymer. In yet another preferred embodiment, the drug is present in an amount from about 1-40 weight %, preferably from about 5-25 weight % and more preferably from about 8-16 weight %, based on the dry weight of the total transdermal system.

According to another aspect of the present invention, there has been provided a method of producing a transdermal drug delivery system. The method comprises the steps of producing a blend of: (a) one or more polymers in a volatile solvent(s); and (b) a therapeutically effective amount of one or more drugs, at least one of which is of low molecular weight and liquid at or about room temperatures. The blend is substantially free of water and liquids having a normal boiling point which is ≧ the normal boiling points of the one or more low molecular weight drugs other than the volatile solvents. The blend is then formed into a polymer matrix and the polymer matrix is dried to remove the volatile solvents. The resulting system is substantially free of water and liquids having a normal boiling point (a) optionally below processing temperatures and (b) ≧ the normal boiling points of the one or more low molecular weight drugs.

According to still another aspect of the present invention, there has been provided a method of treating a human with a therapeutically effective amount of one or more low molecular weight drugs which are liquid at or about room temperatures. The method comprises the steps of: (1) applying to the skin of a human, a transdermal drug delivery system which comprises a blend of: (a) one or more polymers; and (b) a therapeutically effective amount of one or more drugs, at least one of which is of low molecular weight and liquid at or about room temperatures, wherein said system is substantially free of water and liquids having a normal boiling point (i) optionally below processing termperatures and (ii) ≧ the normal boiling points of the one or more low molecular weight drugs; and (2) maintaining the transdermal drug delivery system in contact with the skin for a predetermined length of time sufficient to administer said therapeutically amount of said drug.

According to yet another aspect of the present invention, there has been provided a pressure-sensitive transdermal drug delivery comprising a blend of: (a) one or more polymers having a high shear resistance; and (b) a therapeutically effective amount of one or more drugs, at least one of which is of low molecular weight and liquid at or about room temperatures. The system made according to this embodiment forms a polymer matrix which has sufficient tack and shear for application to a human being. In a preferred embodiment, the high shear resistant polymer has a shear resistance which is ≧50 hours at 4 pounds per square inch (psi) and 72° Fahrenheit (° F.), more preferably ≧100 hours at 4 psi and 72° F., even more preferably ≧100 hours at 8 psi and 72° F.

In another preferred embodiment, the high shear resistant polymer is a higher molecular weight polymer, namely one with a weight average molecular weight in the range of about 600,000 to about 1,000,000 daltons, preferably about 700,000 to about 900,000 daltons, more preferably about 750,000 to about 850,000 daltons. In another preferred embodiment, the high shear resistant polymer is a acrylic-based pressure-sensitive adhesive, especially a higher molecular weight polymer.

According to another aspect of the present invention, there has been provided a method for producing a pressure-sensitive transdermal drug delivery system which includes high shear resistant polymers. The method includes the steps of: (1) producing a blend of: (a) one or more high shear resistant polymers having a shear resistance of ≧50 hours at 4 psi and 72° F. and mixtures thereof; and (b) a therapeutically effective amount of one or more drugs, at least one of which is of low molecular weight and is liquid at or about room temperatures, (2) forming the blend into a shaped form; and (3) drying the shaped form to remove the volatile solvent system to form the transdermal drug delivery system. The system forms a polymer matrix which has sufficient tack and shear for application to a human being.

Further objects, features and advantages of the present invention will become apparent from the detailed description of preferred embodiments which follows.

BRIEF DESCRIPTION OF THE DRAWING

The sole FIGURE is a schematic cross sectional view of the transdermal drug delivery system according to one embodiment of the present invention.

DETAILED DESCRIPTION OF THE PREFERRED EMBODIMENTS

Figure 1:
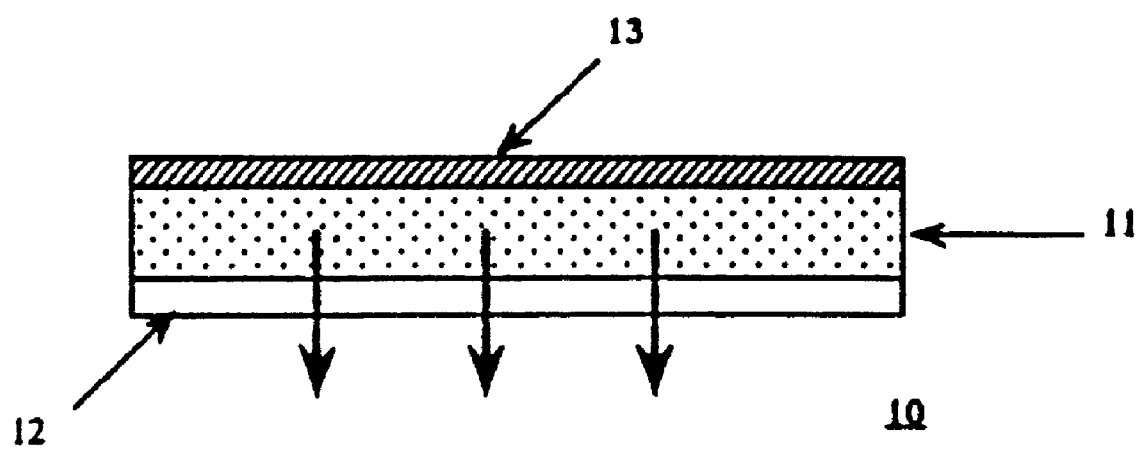

One aspect of the present invention comprises a transdermal drug delivery system which contains a low molecular weight drug, which is liquid at or about room temperatures, and does not require the use of liquids such as water, enhancers or other solvents as is typically used in known transdermal delivery systems.

As used herein, the term "drug," and its equivalents, "bioactive agent," and "medicament" are intended to have the broadest meaning as including any therapeutically, prophylactically and/or pharmacologically or physiologically beneficial active substance, or mixture thereof, which is delivered to a living organism to produce a desired, usually beneficial, effect.

More specifically, any drug which is capable of producing a pharmacological response, localized or systemic, irrespective of whether therapeutic, diagnostic, or prophylactic in nature, in plants or animals is within the contemplation of the invention. Also within the invention are such bioactive agents as pesticides, insect repellents, sun screens, cosmetic agents, etc. It should be noted that the drugs and/or bioactive agents may be used singularly or as a mixture of two or more such agents, and in amounts sufficient to prevent, cure, diagnose or treat a disease or other condition, as the case may be.

Any drug which is liquid at or about room temperatures can be used according to the present invention. As used herein, the term "of low molecular weight and liquid at or about room temperatures" is defined to include any drug which has a melting point such that it normally exists as a liquid at or about room temperatures. This term generally encompasses low molecular weight drugs having a molecular weight of less than about 300 daltons. However, any molecular weight drug can be used in the present invention as long as it normally exists as liquid at or about room temperatures. Conversely, any low molecular weight drug which is not liquid at or about room temperatures is not encompassed by this term. A drug which is of low molecular weight and liquid at or about room temperatures is generally in its free-base or free-acid form, and, as such, is encompassed by this term. The term "of low molecular weight . . . about room temperatures" includes all liquid bioactive agents that would appreciably evaporate or decompose during typical drying temperatures used to remove volatile solvents during processing.

Preferred drugs include selegiline, nitroglycerin, nicotine, ciclopirox olamine, tolbuterol, propanolol, bupranolol, arecolin, methamphetamin, ethosuximide, melproic acid, prilocaine, dyclonine, valproic acid and amphetamine. An especially preferred drug is selegiline. Mixtures of more than one drug can also be used according to the present invention. The second drug need not be one that is normally liquid at or about room temperatures.

The drug is used in a "therapeutically effective amount." This term means that the concentration of the drug is such that in the composition it results in a therapeutic level of drug delivered through the skin over the term that the transdermal dosage form is to be used, preferably with zero order kinetics. Such delivery is dependent on a great number of variables including the drug, the time period for which the individual dosage unit is to be used, the flux rate of the drug from the system and a number of other variables. The amount of drug needed can be experimentally determined based on the flux rate of the drug through the system and through the skin when used with and without enhancers. Having determined the flux rate needed, the transdermal delivery system is designed so that the release rate over the period of time of therapeutic use will be at least equal to the flux rate. Of course, the surface area of the transdermal delivery system also affects the delivery of the drug from the system through the skin. For example when the one or more drugs includes selegiline, the delivery of the selegiline from the system through intact skin in humans ranges between 0.1 and 2.5 mg/cm$^2$/day. When the one or more drugs includes nicotine, the delivery of the nicotine from the system through intact skin in humans ranges between 0.1 and 2.5 mg/cm$^2$ day. When the one or more drugs includes nitroglycerin, the delivery of the nitroglycerine from the system through intact skin in humans ranges between 0.05 and 2.5 mg/cm$^2$/day. For drugs which can exist either as a free-base or salt thereof, the free base form is preferred to increase the rate of delivery through the skin.

As used herein, the term "enhancer" is defined to include agents known to accelerate the delivery of the drug through the skin. These agents have been referred to as skin penetration enhancers, accelerants, adjuvants, and sorption promoters, and are collectively referred to as "enhancers." This class of agents includes those with diverse mechanisms of action including those which have the function of improving the solubility and diffusibility of the drug within the polymer matrix and those which improve percutaneous absorption, for example, by changing the ability of the stratum corneum to retain moisture, softening the skin, improving the skin's permeability, acting as penetration assistants or hair-follicle openers or changing the state of the skin including the boundary layer. Some of these agents have more than one mechanism of action, but in essence they are generally thought to serve to enhance the delivery of the drug.

Some examples of enhancers are polyhydric alcohols such as dipropylene glycol, propylene glycol, and polyethylene glycol which enhance drug solubility; oils such as olive oil, squalene, and lanolin; polyethylene glycol ethers and fatty ethers such as cetyl ether and oleyl ether; fatty acid esters such as isopropyl myristate which enhance drug diffusibility; fatty acid alcohols such as oleyl alcohol; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, isopropyl palmitate, oleamide, polyoxyethylene (4) lauryl ether, polyoxyethylene (2) oleyl ether and polyoxyethylene (10) oleyl ether sold under the trademarks Brij 30, 93 and 97 by ICI Americas, Inc., and polysorbate 20 sold under the trademark Tween 20 by ICI Americas, Inc.

As used herein, "co-solvents" are defined to include agents which increase the solubility of a drug in the polymer matrix. Co-solvents include lecithin, retinol derivatives, tocopherol, dipropylene glycol, triacetin, propylene glycol, saturated and unsaturated fatty acids, mineral oil, silicone fluid, alcohols, butyl benzyl phthalate, butylene glycol, glycerin and the like.

The present inventors have found that due to the liquid nature of the low molecular weight drug, the drug can be incorporated into a transdermal composition without the requirement of additional liquids such as enhancers, as defined above. In addition, due to solubility of the low molecular weight drugs in the transdermal drug delivery system, the low molecular weight drug functions, to a certain degree, as a plasticizer of the one or more polymers of the composition. Thus, co-solvents which are required for drugs with limited solubility are not required in the present invention. This plasticizing effect of the drug is the topic of another embodiment of the present invention disclosed in more detail below.

The present inventors have also found that due to the volatile nature of the relatively low normal boiling point of the drug, the use of water and higher normal boiling point liquids, such as the volatile processing solvents, the enhancers or co-solvents described above, lead to loss of the drug by evaporation during the processing of the transdermal composition. This is especially important where the liquids have boiling points at about or below processing temperatures, especially in the case of the processing solvents. As explained above, a transdermal drug delivery system which is substantially free of any liquids other than the low molecular weight drug(s) provides for less evaporation of the drug during production of the transdermal device and lower cost due to the simpler composition. As used herein, "liquids having a normal boiling point which is about $\geq$ the normal boiling points of the one or more drugs" is defined to include enhancers, co-solvents, processing solvents and any other liquid additives which have normal boiling points greater that the boiling point of the low molecular weight drug being used, especially those having boiling points below the processing temperatures.

As used herein, "substantially free of water and liquids" is defined to comprehend either no or insufficient quantities of water or other liquids to cause substantial evaporation of the drug during production and materially affect desired properties of the transdermal system. Such water and liquids are generally present in an amount, based on the dry weight of the total transdermal system, of less than 10 weight %, and more preferably less than 5 weight %, and even more preferably essentially absent.

The transdermal drug delivery system of the present invention further includes a mixture of one or more polymers blended in with the low molecular weight drug. The terms "blend" and "mixture" are used herein to mean that there is no, or substantially no, chemical reaction or cross-linking (other than simple H-bonding) between the different polymers in the polymer matrix.

As used herein, the term "one or more polymers" is defined to mean that one or a multiple number (e.g., 2, 3 or more) polymers can be used as the polymer matrix of the present invention. There is theoretically no limit to the number of individual polymers which may be used in the transdermal composition of the present invention.

Selection of the particular polymer composition is governed in large part by the desired rate of delivery of the drug. Those skilled in the art can readily determine the rate of drug delivery from the transdermal composition in order to select a suitable combination of polymers for a particular application. Combinations of polymers based on their differing solubility parameters can be used, such as those described in parent application Ser. No. 07/722,342 which is expressly incorporated by reference in its entirety. Various techniques can be used to determine the rate of delivery of the drug from the polymer matrix. Illustratively, the rate of delivery can be determined by measuring the transfer of the selected drug from one chamber to another through cadaver skin over time, and calculating, from the obtained data, the drug delivery or flux rate.

In a preferred embodiment of the present invention, at least one of the one or more polymers is a pressure-sensitive adhesive, forming an adhesive polymer system. As used herein, the term "pressure-sensitive adhesive" refers to a viscoelastic material which adheres instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizer or other additives. The term pressure-sensitive adhesive also includes mixtures of different polymers and mixtures of polymers, such as polyisobutylenes (PIB) of different molecular weights, the resultant mixtures being a pressure-sensitive adhesive. In the last case, the polymers of lower molecular weight in the mixture are not considered to be "tackifiers," said term being reserved for additives which differ other than in molecular weight from the polymers to which they are added.

The adhesive polymer system embodiment is preferably formulated so that it is a pressure-sensitive adhesive at or about room temperatures and has other desirable characteristics for adhesives used in the transdermal-drug delivery art. Such characteristics include good adherence to skin, ability to be peeled or otherwise removed without substantial trauma to the skin, retention of tack with aging, etc. In general, the adhesive polymer system should have a glass transition temperature ($T_g$), measured using a differential scanning calorimeter, of between about −70° C. and 0° C.

In a particularly preferred embodiment, the adhesive polymer system comprises an acrylic-based polymer. As used herein the term "acrylic-based" means any polyacrylate, polyacrylic and acrylic adhesive. The amount of acrylic-based polymer (hereinafter broadly referred to as a polyacrylate) can range from about 10 to about 90 weight %, preferably about 25 to about 80 weight %, and more preferably about 40 to about 70 weight % based on the dry weight of the total transdermal system with the amount of polyacrylate being dependent on the amount of the low molecular weight drug used.

The polyacrylate polymer can be any of the homopolymers, copolymers, terpolymers, and the like of various acrylic acids or esters. The polyacrylates useful in practicing the invention are polymers of one or more monomers of acrylic acids and other copolymerizable monomers. The polyacrylates also include copolymers of alkyl acrylates and/or methacrylates and/or copolymerizable secondary monomers or monomers with functional groups. By varying the amount of each type of monomer added, the cohesive properties of the resulting polyacrylate can be changed as is known in the art. In general, the polyacrylate is composed of at least 50% by weight of an acrylate or alkyl acrylate monomer, from 0 to 20% of a functional monomer copolymerizable with the acrylate, and from 0 to 40% of other monomers.

Further details and examples of acrylic adhesives which are suitable in the practice of the invention are described in Satas, "Acrylic Adhesives," *Handbook of Pressure-Sensitive Adhesive Technology*, 2nd ed., pp. 396-456 (D. Satas, ed.), Van Nostrand Reinhold, New York (1989), which is expressly incorporated by reference in its entirety.

Suitable acrylic adhesives are commercially available and include the polyacrylate adhesives sold under the trademarks Duro-Tak 80-1194, 80-1196, 80-1197, 87-2287, 87-2516 and 87-2852 by National Starch and Chemical Corporation, Bridgewater, N.J. Other suitable acrylic adhesives are those sold under the trademarks Gelva-Multipolymer Solution GMS 737, 788, 1151 and 1430 (Monsanto; St. Louis, Mo.). Still other suitable acrylic adhesives are those sold under the trademark Morstik 703, 707, 705, 607, 709 and 605, all available from Morton International Corporation.

In another preferred embodiment, the polymers selected are a blend of an acrylic-based and rubber-based polymer. As used herein, the term "rubber-based" refers to a viscoelastic material which contains at least one natural or synthetic elastomeric polymer. Suitable rubber-based polymers include silicone-based polymers, natural rubber, hydrocarbon polymers such as natural and synthetic polyisoprene, polybutylene and polyisobutylene, styrene/butadiene polymers, styrene-isoprene-styrene block copolymers, hydrocarbon polymers such as butyl rubber, halogen-containing polymers such as polyacrylo-nitrile, polytetrafluoroethylene, polyvinylchloride, polyvinylidene chloride, ethylene-vinyl acetate, polyvinyl alcohols, polyvinyl acetates, polyvinylpyrrolidones and polychloroprene and other copolymers thereof. In a preferred embodiment, the rubber-based polymer is a pressure-sensitive adhesive.

In another preferred embodiment, the polymer adhesive is a blend of the polyacrylate described above and a silicone-based polymers (hereinafter referred to broadly as a polysiloxane). The polysiloxanes are present in an amount of about 1 to about 70 weight %, preferably about 20 to about 60 weight %, and more preferably about 20 to about 40 weight %, based on the dry weight of the total transdermal system.

Suitable polysiloxanes include silicone pressure-sensitive adhesives which are based on two major components: a polymer, or elastomer, and a tackifying resin. The polysiloxane adhesive is usually prepared by cross-linking the elastomer, typically a high molecular weight polydiorganosiloxane, with the resin, to produce a three-dimensional siloxane structure, via a condensation reaction in an appropriate organic solvent. The ratio of resin to elastomer is the most important factor which can be adjusted in order to modify the physical properties of polysiloxane adhesives. Sobieski, et al., "Silicone Pressure Sensitive Adhesives," *Handbook of Pressure-Sensitive Adhesive Technology*, 2nd ed., pp. 508-517 (D. Satas, ed.), Van Nostrand Reinhold, New York (1989).

Further details and examples of silicone pressure-sensitive adhesives which are useful in the practice of this invention are described in the following U.S. Pat. Nos. 4,591,622; 4,584, 355; 4,585,836; and 4,655,767, all expressly incorporated by reference in their entireties.

Suitable silicone pressure-sensitive adhesives are commercially available and include the silicone adhesives sold under the trademarks BIO-PSA X7-3027, X7-4203, Q7-4503, X7-4603, X7-4301, X7-4303, X7-4919, X7-2685, X7-4403, Q7-4501 and X7-3122 by Dow Corning Corporation, Medical Products, Midland, Mich.

To summarize, the preferred and optimum compositions for the polyacrylate and polysiloxane embodiments are as follows:

TABLE 1

PERCENT BY WEIGHT

| Component | Preferred Range | More Preferred Range | Most Preferred Range |
|---|---|---|---|
| Polyacrylate | about 10–90 | about 25–80 | about 40–70 |
| Polysiloxane | about 1–70 | about 20–60 | about 20–40 |
| Low Molecular Weight Drug | about 1–40 | about 5–25 | about 8–16 |

The transdermal drug delivery system of the present invention may further be provided with various thickeners, fillers and other additives known for use with transdermal drug delivery systems. Where the composition tends to absorb water, hydrophilic substances are especially useful. One type of hydrophilic substance which has been successfully employed is clay. The addition of clay has been found to improve adhesiveness in transdermal formulations without reducing the rate of drug delivery. Suitable clays include kaolinites such as baolinite, anauxite, dickite and nacrite, montmorillonites such as montmorillonite, bentonite, berdellite and montronite, illites/muscovites such as illite and glauconite, chlorites, polygorshites such as attapulgite, halloysite, metabolloysite, allophane and aluminum silicate clays.

In a device aspect of the invention, the preferred pressure-sensitive adhesive composition embodiment can be used as an adhesive portion of any transdermal drug delivery system (e.g., a reservoir device) or it can comprise an adhesive monolithic device. Of course, the principles of the invention would still apply to embodiments where the transdermal drug delivery composition is not a pressure-sensitive adhesive and comprises a drug reservoir.

Reference to the sole FIGURE shows a schematic illustration of an adhesive monolithic device embodiment of the invention 10. The transdermal drug delivery system comprises a monolithic body 11 of a defined geometric shape with a protective release liner 12 on one side of monolithic body 11 and a backing layer 13 on the other side. Removal of the release liner 12 exposes the pressure-sensitive polymer adhesive composition which functions both as the drug carrier matrix and as the means of applying the system to the patient.

A device, or individual dosage unit, of the present invention can be produced in any manner known to those of skill in the art. After the dermal composition is formed, it may be brought into contact with the backing layer in any manner known to those of skill in the art. Such techniques include calendar coating, hot melt coating, solution coating, etc. Of course, backing materials are well known in the art and can comprise plastic films of polyethylene, vinyl acetate resins, polyester, polypropylene, BAREX®, ethylene/vinyl acetate copolymers, polyvinyl chloride, polyurethane, and the like, metal foils, non-woven fabric, cloth, coextrusions or laminations of the above and commercially available laminates. The backing material generally has a thickness in the range of 2 to 1000 micrometers and the dermal composition is generally disposed on backing material in a thickness ranging from about 12 to 250 micrometers thick.

Suitable release liners are also well known in the art and include the commercially available products of Release International designated Bio-Releases liner and Syl-off® 7610 liner. For preferred embodiments in which a polysiloxane is part of the multiple polymer adhesive system, the release liner must be compatible with the silicone adhesive. An example of a suitable commercially available liner is 3M's 1022 Scotch-Pak.

The configuration of the transdermal delivery system of the present invention can be in any shape or size as is necessary or desirable. Illustratively, a single dosage unit may have a surface area in the range of 1 to 200 cm$^2$. Preferred sizes are from 5 to 60 cm$^2$.

According to another aspect of the present invention, a method of making a transdermal drug delivery system is disclosed. One or more polymers are blended to result in a composition, preferably a pressure-sensitive adhesive composition, which controls delivery of the incorporated low molecular weight drug into and through the epidermis. The term "blending" of course, incorporates choosing the appropriate polymer components, and the proportions thereof, to achieve the desired effect.

In a preferred embodiment of the invention, a transdermal drug delivery system is prepared by mixing one or more polymers, preferably polyacrylate and polysiloxane, a liquid low molecular weight drug, non-liquid fillers and excipients if needed, in appropriate low normal boiling point volatile solvent(s). The mixture is then casted and the solvent(s) are removed by evaporation to form a film.

As used herein, "volatile solvent(s)" are defined as solvents for keeping the polymers in solution until they are evaporated off in the drying phase. The volatile solvents do not include water and generally have a normal boiling point which is less than that of the low molecular weight drug being incorporated into the transdermal system. Volatile solvents include, but are not limited to, alcohols such as isopropanol and ethanol; aromatics such as xylenes and toluene; aliphatics such as hexane, cyclohexane, and heptane; and alkanoic acid esters such as ethyl acetate and butyl acetate.

Solvents which have a boiling point which is greater than that of the drug may be used in combination with the low boiling point solvents. However, the amount of the solvent used with the low boiling point solvent must be low enough that the high boiling point solvent which will remain in the composition after drying will not materially affect the performance of the transdermal drug delivery system.

Typically pressure senstive adhesives are supplied either as water-based emulsions or solutions in volatile organic solvents. Since water is to be excluded from the processing system, the pressure sensitive adhesives are used in solutions of organic solvents. The mixtures are combined with the appropriate drugs and other ingredients and then cast into shaped forms, with or without cross-linking, by evaporation of the volatile solvents. An exemplary general method of preparation is as follows:

1. Appropriate amounts of polymers, low molecular weight drugs and low boiling point solvent(s) are combined and thoroughly mixed together in a vessel.

2. The formulation is then transferred to a coating operation where it is coated onto a protective release liner at a controlled specified thickness. The coated product is then passed through an oven in order to drive off the low boiling point solvents.

3. The dried product on the release liner is then joined to the backing material and wound into rolls for storage.

4. Appropriate size and shape "systems" are die-cut from the roll material and then pouched.

The order of steps, the amount of the ingredients, and the amount and time of agitation or mixing may be important process variables which will depend on the specific polymers used in the formulation. These factors can be adjusted by those skilled in the art using the present specification as a guide, while keeping in mind the object of providing a uniform product. It is believed that a number of other methods, including changing some of the order of steps, can be carried out and will give desirable results. In the case of selegeline base having a boiling point of 92°-93°Celsius (°C.), the drying is conveniently done at 130° to 160° F.

In addition to having various shapes, the dosage units produced may come in various sizes. A surface area in the range of 1 to 200 square centimeters is contemplated, and the presently preferred sizes are: 5, 10, 15, 20, 30, 30 and 60 square centimeters.

EXAMPLE 1

A selegiline-polymer mixture was prepared by combining 3.0 parts of free-base selegiline and 23.33 parts of a polysiloxane-solvent solution (BIO-PSA X7-4501) and 8.82 parts of an acrylic-solvent solution (Duro-Tak 87-2852) in an appropriate container, and then mixing well until the mixture was completely homogenous. The resulting composition was dried at room temperature for four minutes and then at 50° C. for four minutes, which was sufficient to drive off the low boiling point process solvents. The resulting composition has the ingredient concentrations on a "dry" basis, that is, after the removal of the volatile process solvents.

| COMPONENT | PERCENT BY WEIGHT |
|---|---|
| Polysiloxane Adhesive (BIO-PSA X7-4501) | 70.0 |
| Polyacrylate Adhesive (Duro-Tak 87-2852) | 15.0 |
| Selegiline base | 15.0 |
| | 100.0 |

In the following examples, the method of Example 1 was used with the appropriate amounts of starting materials to yield compositions having the following ingredient concentrations.

TABLE 2

| Examples Component | Ex. 2 | Ex. 3 | Ex. 4 | Ex. 5 |
|---|---|---|---|---|
| | | Percent by Weight | | |
| Polysiloxane Adhesive (BIO-PSA X7-4501) | 32 | 28 | 70 | 24 |
| Polyacrylate Adhesive (Duro-Tak 87-2852) | 60 | 60 | 15 | 60 |
| Selegiline Base | 8 | 12 | 15 | 16 |

TABLE 3

| Examples Component | Ex. 6 | Ex. 7 | Ex. 8 | Ex. 9 | Ex. 10 |
|---|---|---|---|---|---|
| | | | Percent by Weight | | |
| Polysiloxane Adhesive (BIO-PSA X7-4501) | 20 | 16 | 39 | 54 | 18 |
| Polyacrylate Adhesive (Duro-Tak 87-2852) | 60 | 60 | 45 | 30 | 60 |
| Selegiline Base | 20 | 24 | 16 | 16 | 22 |

In another embodiment of the present invention, the present inventors have discovered that when polymers having a high shear resistance are used in the polymer matrix in a transdermal drug delivery system, the shear resistance of the resulting polymer matrix is not significantly reduced due to the plasticizing effect of liquid drugs. As described above, the plasticizing effect of liquid drugs in conventional transdermal drug delivery system, resulted in a marked decrease in shear resistance of the polymer matrix. This decreased shear resistance leads to legging or gumminess of the polymer to the point that it is no longer suitable for wear.

As used herein, "legs" are adhesive strings that can be seen when an adhesive flows. Legging is defined as the removal from the adhesive surface of small amounts of adhesive which in turn remains on the application surface upon removal of the product. On human skin, this legginess or gumminess shows up as a residue upon patch removal. "Legging" or "gumminess," is further defined when the shear resistance of the pressure-sensitive transdermal system, is such that the transdermal system will slip after application or leave a residue upon removal.

As used herein, "shear resistance" is defined as the force required to pull a pressure-sensitive tape for a standard flat surface in a direction parallel to the flat surface. In the present invention, the flat surface used to determine the shear resistance is a polished stainless steel plate.

Before the present invention, many attempts had been made to reduce the legging effects of liquid drugs with only limited success. However, the present inventors discovered that generally by using high shear resistant polymer(s) as a "starting point," the plasticizing effect of the drug does not result in significant decreases in the shear resistance of the pressure-sensitive adhesive to the point of legging or gumminess. This use of polymer(s) having high shear resistance, results in a transdermal drug delivery system which has outstanding wear properties.

As used herein, a polymer matrix for a transdermal system of the present invention has "high shear resistance" if it does not slip after application or does not leave a significant residue after removal. The pressure-sensitive adhesive according to this embodiment of the present invention generally has a shear resistance of about $\geq 50$ hours at 4 psi and 72° F., preferably about $\geq 100$ hours at 4 psi and 72° F. and more preferably about $\geq 100$ hours at 8 psi and 72° F.

In addition to offsetting the plasticizing effect of the liquid drugs, the present inventors discovered unexpectedly, that the use of a high shear resistant polymers resulted in an increased ability for solubilization of the drug in the polymer matrix of the transdermal drug delivery system. This surprising discovery permits higher loadings of the drug in the adhesive than previously envisioned. As used herein, "high loading" is defined as having a drug concentration in the finished transdermal drug delivery system of about 25-40 weight %, based on the dry weight of the total transdermal system. Any polymer having a high shear resistance and capable of being used as a polymer matrix in transdermal drug delivery systems may be used according to the present invention. The selection of a suitable polymer can be determined by one of ordinary skill in the art using the present specification as a guide.

The shear resistance of the polymer is generally related to the molecular weight of the polymer. A polymer having a weight average molecular weight generally in the range of about 600,000 to about 1,000,000 daltons, preferably about 700,000 to about 900,000 daltons, more preferably about 750,000 to about 850,000 daltons can be used in the present invention. However, any polymer which has a sufficient shear resistance as defined above can be used in the present invention, regardless of molecular weight.

In a preferred embodiment, the high shear resistance polymer is a pressure-sensitive acrylic-based adhesive. The term acrylic-based is defined as above. Any acrylic polymer which has a sufficiently high shear resistance can be used in the present invention. A preferred commercially available acrylic polymer is Duro-Tak 87-2852, which has also been described above. Other preferred commercially available acrylic polymers are Gelva Multipolymer Solution 737 and Duro-Tak 87-2194. Other polymers, e.g. silicone polymers, polyisobutylene, having a sufficiently high shear strength may also be used in the present inventors. Example of preferred silicone adhesive polymers include BIO-PSA Q7-4503, Q7-4501 and X7-4601.

Any additional additives such as enhancers, co-solvents, excipients and fillers as described above, can generally be used in this high shear resistance aspect of the present invention. However, in a preferred embodiment the only components present in a substantial amount are the low molecular weight drug and the high shear resistance polymer, wherein the drug comprises between 8-40 weight %, based on the dry weight of the total transdermal system.

Other polymers which are not high shear resistant polymers can also be used in the high shear resistance embodiment of the present invention. However, the amount of these polymers added should be kept below an amount which would lead legginess or gumminess problems as noted above. One of ordinary skill in the art using the present specification as a guide, would be able to determine through routine experimentation the maximum amount of non high shear resistant polymers which can be used.

An exemplary general method of preparation for this aspect of the present invention is as follows:

1. Appropriate amounts of a high shear resistance polymer, low molecular weight drugs, organic solvent(s) and other liquid or solid additives are combined and thoroughly mixed together in a vessel.

2. The formulation is then transferred to a coating operation where it is coated onto a protective release liner at a controlled specified thickness. The coated product is then passed through an oven in order to drive off all volatile processing solvents.

3. The dried product on the release liner is then joined to the backing material and wound into rolls for storage.

4. Appropriate size and shape "systems" are die-cut from the roll material and then pouched.

As noted above, the order of steps, the amount of the ingredients, and the amount and time of agitation or mixing may be important process variables which will depend on the specific polymers used in the formulation. These factors can be adjusted by those skilled in the art, while keeping in mind the object of providing a uniform product. It is believed that a number of other methods, including changing some of the order of steps, can be carried out and will give desirable results.

EXAMPLES 11-37

Transdermal drug delivery systems according to the high shear resistance embodiment of the present invention were prepared according to the method given above for Examples 1-10, except for the different starting materials, which are set forth below in Tables 4-6.

All of the transdermal drug delivery systems in Examples 11-37 exhibited excellent adhesivity and drug loading properties, without the gumminess or legginess as described above.

TABLE 4

| Raw Material | % (Weight/Weight) of Final Composition | | | | | | | | | |
|---|---|---|---|---|---|---|---|---|---|---|
| Example | 11 | 12 | 13 | 14 | 15 | 16 | 17 | 18 | 19 | 20 |
| Polysiloxane Adhesive (BIO-PSA Q7-4501) | 30 | 15 | 15 | 60 | 60 | 50 | — | — | — | 10 |
| Polysiloxane Adhesive (BIO-PSA X7-4601) | — | 15 | 15 | — | — | 10 | — | — | — | — |
| Polyacrylate Adhesive (Duro-Tak 87-2852) | 65 | 65 | 50 | — | 10 | 10 | 75 | 60 | 75 | 40 |
| Polyacrylate Adhesive (GMS 737) | — | — | — | 20 | 10 | 10 | — | 10 | 10 | 20 |
| Nicotine Base | 5 | 5 | 20 | 20 | 20 | 20 | 25 | 30 | 15 | 30 |

TABLE 5

| Raw Material | % (Weight/Weight) of Final Composition | | | | | | | | |
|---|---|---|---|---|---|---|---|---|---|
| Example | 21 | 22 | 23 | 24 | 25 | 26 | 27 | 28 | 29 |
| Polysiloxane Adhesive (BIO-PSA Q7-4503) | 30 | 20 | 30 | 25 | 25 | 20 | — | — | — |
| Polyacrylate Adhesive (Duro-Tak 87-2852) | 50 | 48 | 45 | 40 | 15 | 50 | 75 | 70 | 50 |
| Polyacrylate Adhesive (Duro-Tak 87-2194) | — | — | — | 15 | 40 | — | — | — | 20 |
| Co-Solvent (DPG) | — | 4 | 3 | — | — | — | — | 7 | 8 |
| Nitroglycerine Adhesive | 20 | 20 | 20 | 20 | 20 | 30 | 20 | 20 | 20 |
| Clay (Bentonite) | 5 | 5 | 20 | 20 | 20 | 20 | 25 | 30 | 15 |

TABLE 6

| Raw Material | % (Weight/Weight) of Final Composition | | | | | | | |
|---|---|---|---|---|---|---|---|---|
| Example | 30 | 31 | 32 | 33 | 34 | 35 | 36 | 37 |
| Polysiloxane Adhesive (BIO-PSA Q7-4501) | 20 | 20 | 10 | — | — | 20 | — | — |
| Polyacrylate Adhesive (Duro-Tak 87-2852) | 40 | 40 | 70 | 70 | 60 | 40 | 60 | 80 |
| Co-Solvent (DPG) | — | — | — | — | — | 8 | 10 | 4 |
| Dyclonine Base | 10 | 20 | 10 | 15 | 10 | 12 | 10 | 12 |
| Prilocaine Base | 30 | 20 | 10 | 15 | 30 | 20 | 20 | 4 |

Other embodiments of the invention will be apparent to those skilled in the art from consideration of the specification and practice of the invention disclosed herein. It is intended that the specification be considered as exemplary only, with the true scope and spirit of the invention being indicated by the following claims.

What is claimed is:

1. A transdermal drug delivery system comprising a blend of:
   (a) one or more polymers; and
   (b) a therapeutically effective amount of one or more drugs, at least one of which is a low molecular weight drug with a molecular weight of less than about 300 daltons and is liquid at or about room temperatures, and wherein said one or more drugs comprises amphetamine, wherein said system is substantially free of water and liquids having a boiling point (i) below processing temperatures and (ii) equal to or greater than the normal boiling points of the at least one low molecular weight drug; and, wherein at least one of said one or more polymers is a high shear resistant acrylic-based pressure-sensitive adhesive polymer having a shear resistance which is greater than or equal to 50 hours at 8 pounds per square inch and 72° Fahrenheit.

2. A pressure-sensitive adhesive transdermal drug delivery system suitable for transdermal drug delivery comprising a blend of:
  (a) one or more solvent-based high shear resistant acrylic-based polymers having a shear resistance which is greater than or equal to 50 hours at 8 pounds per square inch and 72° Fahrenheit, and a weight average molecular weight in the range of about 600,000 to about 1,000,000 daltons; and
  (b) a therapeutically effective amount of one or more drugs, at least one of which is a low molecular weight drug with a molecular weight of less than about 300 daltons and is liquid at or about room temperatures, wherein the transdermal drug delivery system forms a polymer matrix which has sufficient tack and shear to remain in place under conditions of use.

3. A pressure-sensitive transdermal drug delivery system as claimed in claim 2, wherein the one or more high shear resistant acrylic-based polymers have a weight average molecular weight in the range of about 700,000 to about 900,000 daltons.

4. A pressure-sensitive transdermal drug delivery system as claimed in claim 3, wherein the one or more high shear resistant acrylic-based polymers have a weight average molecular weight in the range of about 750,000 to about 850,000 daltons.

5. A method of producing a pressure-sensitive transdermal drug delivery system suitable for a transdermal drug delivery system, comprising the steps of:
  (1) producing a blend of:
    (a) one or more polymers, wherein at least one of said one or more polymers is a solvent-based high shear resistant acrylic-based pressure-sensitive adhesive polymer; and
    (b) a therapeutically effective amount of one or more drugs, at least one of which is a low molecular weight drug with a molecular weight of less than about 300 daltons and is liquid at or about room temperatures, wherein the blend is in a solvent system;
  (2) forming the blend into a polymer matrix; and
  (3) drying the polymer matrix to remove the solvent system to form the transdermal drug delivery system, wherein the system forms a polymer matrix which has sufficient tack and shear for application to a human being.

6. A pressure-sensitive transdermal drug delivery system for transdermal drug delivery as claimed in claim 2, wherein the one or more drugs comprise amphetamine.

\* \* \* \* \*